US 6,750,899 B1

(12) United States Patent
Fishbaine et al.

(10) Patent No.: US 6,750,899 B1
(45) Date of Patent: Jun. 15, 2004

(54) SOLDER PASTE INSPECTION SYSTEM

(75) Inventors: David Fishbaine, Minnetonka, MN (US); Timothy A. Skunes, Mahtomedi, MN (US); Eric P. Rudd, Hopkins, MN (US); David M. Kranz, Minneapolis, MN (US); Carl E. Haugan, St. Paul, MN (US)

(73) Assignee: CyberOptics Corporation, Golden Valley, MN (US)

( * ) Notice: Subject to any disclaimer, the term of this patent is extended or adjusted under 35 U.S.C. 154(b) by 0 days.

(21) Appl. No.: 09/524,133

(22) Filed: Mar. 10, 2000

Related U.S. Application Data

(60) Provisional application No. 60/175,049, filed on Jan. 7, 2000.

(51) Int. Cl.$^7$ .............................. H04N 7/18; G06K 9/00; G01B 11/00
(52) U.S. Cl. ..................... 348/126; 382/147; 356/395
(58) Field of Search .......................... 348/126, 87, 94, 348/95; 228/105; 382/147; 356/395, 237.2, 608; 378/58; 386/106

(56) References Cited

U.S. PATENT DOCUMENTS

| | | | |
|---|---|---|---|
| 3,777,061 A | 12/1973 | Takemura | 178/5.4 R |
| 3,995,107 A | 11/1976 | Woywood | 178/7.1 |
| 4,541,010 A | 9/1985 | Alston | 358/44 |
| 4,598,321 A | 7/1986 | Elabd et al. | 358/213 |
| 4,641,972 A | 2/1987 | Halioua et al. | 356/376 |
| 4,643,565 A | 2/1987 | Goto | 356/24 |
| 4,677,473 A | 6/1987 | Okamoto et al. | 358/101 |

(List continued on next page.)

FOREIGN PATENT DOCUMENTS

| | | |
|---|---|---|
| DE | 19 511 160 A1 | 3/1995 |
| WO | WO 98/59490 | 6/1998 |
| WO | WO 0106210 A1 | 1/2001 |
| WO | WO 0154058 A2 | 7/2001 |

OTHER PUBLICATIONS

"Rank Order Morphological Hit–Miss Transform and Its Optical Implementation", by Huiquan et al., ACTA OPTICA SINICA, vol. 19, No. 9, pp. 1256–1263 (Sep. 1999). Translation provided.

"Cognex and Sony Team Develops Machine–Vision Camera", Vision Systems Design, p. 15 (Feb. 1999).

"3–D Profilometry Based on Modulation Measurement", by Likun et al., vol. 19, No. 9, pp. 1–11 (Sep. 1999).

"High Frame Rate Cameras", Princeton Instruments Catalog of High Performance Digital CCD Cameras, 2 pages (Oct. 1994).

"Area Array CCD Image Sensor 1024=1024 Pixels with Antiblooming", CCD Products, Thomson–CSF Semiconducteurs Specifiques, pp. 267–273 (1996).

"Accurate Machine Vision is the 'Telecentric Advantage'", 3 pages from website.

Primary Examiner—Gims Philippe
(74) Attorney, Agent, or Firm—Westman, Champlin & Kelly, P.A.

(57) ABSTRACT

A novel inspection system for inspecting an article of manufacture, such as a printed circuit board, is disclosed, where the system includes a strobed illuminator adapted to project light through a reticle so as to project a pattern of light onto an area of the printed circuit board. A board transport responsively positions the board to at least two distinct positions, where each position corresponding to a different phase of the projected light. Also included is a detector adapted to acquire at least two images of the area, each image corresponding to one of the at least two different phases. An encoder monitors the movement of the board and outputs a position output, and a processor connected to the encoder, the board transport, the illuminator and the detector controlledly energizes the illuminator to expose the area as a function of the position output, the processor co-siting the at least two images and constructing a height map image with the co-sited images.

20 Claims, 4 Drawing Sheets

U.S. PATENT DOCUMENTS

| | | | |
|---|---|---|---|
| 4,835,616 A | 5/1989 | Morcom | 358/213.19 |
| 4,949,172 A | 8/1990 | Hunt et al. | 358/101 |
| 4,963,024 A | 10/1990 | Ulich | 356/342 |
| 4,984,893 A | 1/1991 | Lange | 356/376 |
| 5,135,308 A | 8/1992 | Kuchel | 356/376 |
| 5,278,634 A | 1/1994 | Skunes et al. | 356/400 |
| 5,450,204 A | 9/1995 | Shigeyama et al. | 356/378 |
| 5,450,228 A | 9/1995 | Boardman et al. | 359/209 |
| 5,636,025 A | 6/1997 | Bieman et al. | 356/374 |
| 5,646,733 A | 7/1997 | Bieman | 356/376 |
| 5,862,973 A * | 1/1999 | Wasserman | 228/105 |
| 5,878,152 A * | 3/1999 | Sussman | 382/106 |
| 5,991,461 A | 11/1999 | Schmucker et al. | 382/284 |
| 5,995,232 A * | 11/1999 | Van Der Ven | 356/395 |
| 5,999,266 A | 12/1999 | Takahashi et al. | 356/376 |
| 6,028,673 A * | 2/2000 | Nagasaki et al. | 356/608 |
| 6,081,613 A * | 6/2000 | Ikurumi et al. | 382/147 |
| 6,185,273 B1 * | 2/2001 | Sperschneider | 378/58 |
| 6,201,892 B1 | 3/2001 | Ludlow et al. | 382/149 |
| 6,303,916 B1 | 10/2001 | Gladnick | 250/205 |
| 6,445,813 B1 * | 9/2002 | Ikurumi et al. | 382/147 |
| 6,496,254 B2 * | 12/2002 | Bostrom et al. | 356/237.2 |
| 6,522,777 B1 | 2/2003 | Paulsen et al. | 382/154 |

* cited by examiner

SOLDER PASTE INSPECTION SYSTEM

CROSS-REFERENCE TO CO-PENDING APPLICATION

This application claims priority benefits from U.S. provisional patent application Ser. No. 60/175,049, filed Jan. 7, 2000, and entitled "Improved Inspection Machine".

COPYRIGHT RESERVATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

This invention relates to the field of electronic circuit board manufacture. More particularly, this invention relates to an improved system for inspecting solder paste deposited on a circuit board during manufacture.

BACKGROUND OF THE INVENTION

Circuit boards that carry electronic integrated circuits as well as discrete electronic components are well known. A circuit board substrate is prepared with predetermined conductor paths and pads for receiving the lead of an electronic component such as integrated circuit chips, resistors or capacitors. During the circuit board fabrication process, solder paste bricks are placed onto the board substrate at appropriate positions. The solder paste is usually applied by placing a screen onto the substrate, applying solder paste through the screen openings and removing the screen from the substrate. The circuit board electronic components are then positioned onto the substrate, preferably with a pick and place machine, with leads of the electronic components placed on the respective solder paste bricks. The circuit board is passed through an oven after all of the components are positioned on a substrate to melt the solder paste thus creating an electrical as well as mechanical connection between the components and the substrate.

The size of the solder paste bricks and the accuracy with which they must be placed on the substrate has become increasing smaller and tighter with the increased emphasis on miniaturization in the electronics industry. Solder paste brick heights can be as small as 100 microns and the height of the solder paste brick must often be measured to within 1 percent of the designed height and size. The center-to-center spacing between solder bricks is sometimes 200 microns. Too little solder paste can result in no electrical connection between the lead of an electronic component and the pad of the circuit board substrate. Too much paste can result in bridging and short-circuiting between the leads of a component.

A single circuit board can cost thousands and even tens of thousands of dollars to manufacture. Testing of a circuit board after the fabrication process is complete can detect errors in solder paste placement and component lead connection, but often the only remedy for a faulty board is rejection of the entire board. It is accordingly imperative that a circuit board be inspected during the fabrication process so that improper solder paste placement can be detected prior to the placement of the electronic components onto the substrate. Such in-process solder inspection reduces the cost of failure since expensive components have not yet been placed onto the circuit board.

Current solder paste inspection systems have a number of limitations. First, such systems are typically costly and the cost of the system must be borne by board manufacturing prices, and thus finished circuit board prices. Further, current systems are relatively inflexible when tasked with inspecting features of different levels of detail. Such current systems are unable to measure coarse objects with the same sensor, or optical train, as fine objects. Thus, two different optical trains of differing capabilities are required to provide two levels of resolution and throughput, adding significantly to system cost.

Another limitation of current solder paste inspection systems is their susceptibility to vibration. In these systems, the target must remain in a known position in order to achieve high accuracy measurements. Vibration causes features on the target surface to appear in different places than expected. Such spatial error adversely affects the accuracy and repeatability of solder paste height, volume and area measurements, and can lead to the acceptance of a defective solder brick, or the rejection of an otherwise acceptable brick.

Another limitation of current inspection systems is that of inspection speed. Since in-process solder paste inspection is generally performed in the assembly line, the inspection step itself must be done as quickly as possible in order to minimize the impact of inspection on the assembly line's throughput.

User-friendliness is another limitation of current systems. One example of this limitation is that current solder paste inspection systems require users to program a number of points used by the system to establish a reference plane for solder paste height and volume calculation. Eliminating such user setup would significantly facilitate user interaction with the inspection system.

Finally, traditional solder paste inspection systems use relatively high powered lasers (Class III) for imaging. For safety, the FDA has placed strict safety precautions upon the use of such lasers. These precautions can render use of such devices cumbersome. Thus, there is a current need to provide a solder paste inspection system that does not employ any Class III lasers whatsoever.

SUMMARY OF THE INVENTION

A novel inspection system for inspecting articles of manufacture, such as a printed circuit board is disclosed, where the system includes a strobed illuminator adapted to project light through a reticle so as to project a pattern of light onto an area of the printed circuit board. A transport mechanism responsively positions the board to at least two distinct positions, where each position corresponding to a different phase of the projected light. Also included is a detector adapted to acquire at least two images of the area, each image corresponding to one of the at least two different phases. A position encoder monitors the movement of the board and outputs a position output, and a processor connected to the encoder, the transport mechanism, the strobed illuminator and the detector controlledly energizes the strobed illuminator to expose the area as a function of the position output, the processor co-siting the at least two images and constructing a height map image with the co-sited images. In a preferred embodiment of the present invention and method, the detector is further adapted to acquire an additional image of the area as a function of a position of the target, and the processor operates upon three images of the area to provide the compensated height map. In another embodiment, the illuminator is strobed at least two times within a short period of time, such as two milliseconds, to reduce vibration sensitivity of the system. In another embodiment of the invention, solder paste volume is computed from the acquired images and the height map. Another embodiment provides a low resolution, high speed mode where charge from a plurality of pixels is combined to form a larger effective pixel, for use in high speed applications. Optionally, the height map is de-tilted in order to compensate for physically or algorithmically tilted targets.

DETAILED DESCRIPTION OF THE PREFERRED EMBODIMENTS

Figure 1:
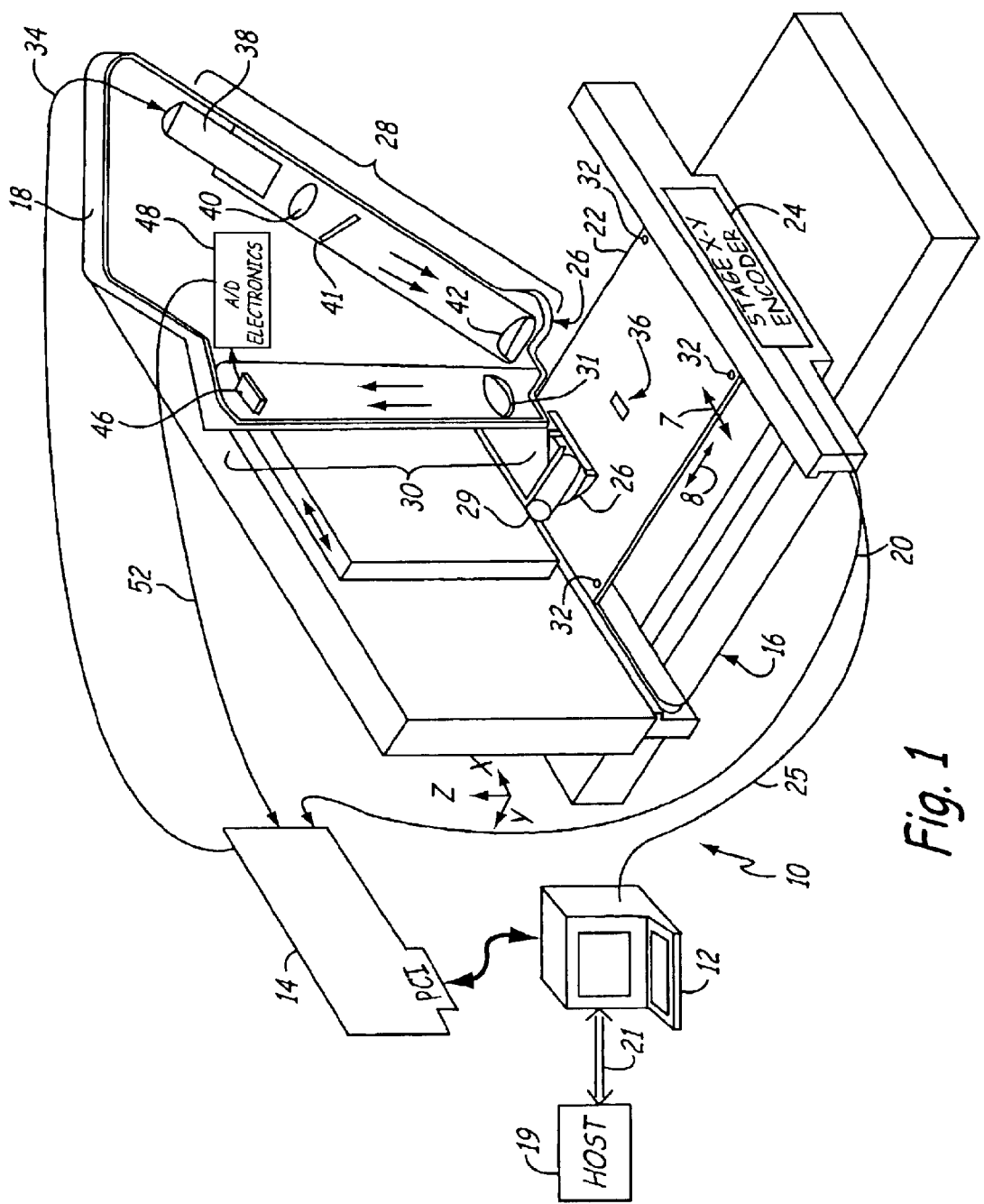
FIG. 1 is a diagrammatic view of a solder paste inspection system in accordance with an embodiment of the present invention.

FIG. 1 shows solder paste inspection system 10, which includes processor 14, X-Y system 16 and optical sensor system 18. Solder paste inspection system 10 is couplable to host device 19 through network 21 or the like, in order to send and receive information related to solder inspection on printed circuit boards. For example, system 10 may receive location information relating to specific solder paste locations, and their respective nominal volume. Preferably, processor 14 is disposed within microcomputer 12, which microcomputer 12 is a known device having an input such as a keyboard, and mouse, and an output in the form of a video monitor. Additionally, microcomputer 12 preferably includes an industry-standard architecture and microprocessor. One example, is a personal computer running a Microsoft Windows® operating system with an Intel Pentium® III processor.

Processor 14 is preferably embodied upon a computer peripheral card with an industry-standard form factor. Further, processor 14 is preferably adapted to couple to microcomputer 12 through a standard Peripheral Component Interconnect (PCI) bus. Processor 14 can then transfer data to and from microcomputer 12 using a known Direct Memory Access (DMA) transfer method to facilitate high-speed data transfer.

Processor 14 receives the digital video data from analog/digital electronics 48 and performs a number of functions on such data. For example, processor 14 triggers sensor system 18 to acquire images based upon encoder information received from encoders 24 through line 20. Processor 14 also communicates with sensor system 18 in order to control its operational mode (i.e. high-resolution vs. high-speed). Processor 14 receives previously digitized video data from sensor system 18 for storage in a frame buffer (not shown). Processor 14 operates upon the digitized video images to correct for defects in the particular CCD array 46 in sensor system 18. Processor 14 is also used to compensate for effects of known optical distortions on the height map. Each of the mentioned functions is described below in more detail.

Processor 14 is coupled to X-Y system 16 through line 20. X-Y system 16 also includes X and Y motors (not shown) which position circuit board 22 in respective X and Y axes. X and Y motors are operably coupled to X and Y encoders (shown diagrammatically at block 24) to provide data indicative of circuit board position along X and Y axes to processor 14. Motion commands are sent over line 25 to system 16. System 16 is extraordinarily stable and its motion is controlled to within approximately one micron over approximately 280 microns of distance travelled. If system 16 is not sufficiently stable, additional processing in the electronics may be needed to provide equivalent accuracy and repeatability. In the preferred embodiment, each of the linear encoders preferably has a resolution of about 0.5 $\mu$m, as can be purchased from Renishaw. Thus, through cooperation, computer 12 and X-Y system 16 precisely move circuit board 22 as desired in the X and Y directions at arrows 7,8, respectively.

Optical sensor system 18 includes camera system 30, projection system 28, circular illuminator 26 and laser range finder 29. Camera system 30 includes camera lens 31, a detector 46 and a set of A/D electronics 48. Projection system 28 includes flashlamp 38, condenser 40, recile 41 and projector 42. All the components within system 18 are fixed within a housing for the system. System 18 is fixed attached to a translation stage (not shown) to provide z movement for focus control.

Figure 2:
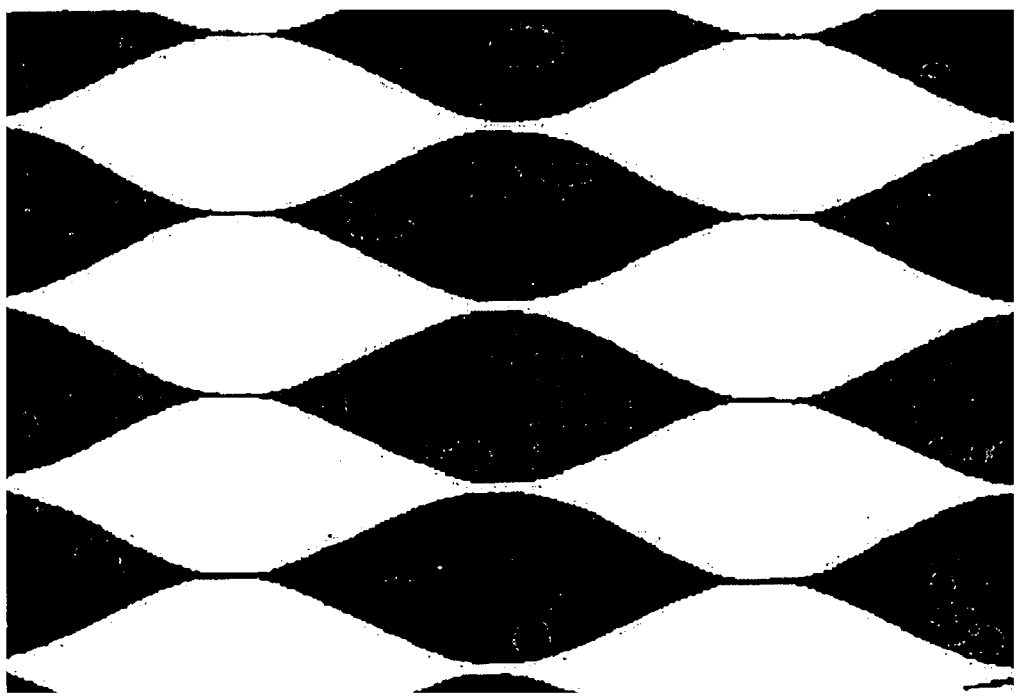
FIG. 2 is a diagram of the astigmatic transmission pattern on the reticle.

Projection system 28, in combination with the stage movement, projects three phases of structured light onto solder paste features 36. Flashlamp 38 is preferably a high-speed strobe lamp filled with xenon gas, projecting broadband white light. A high speed discharge circuit (not shown) within housing 18 drives lamp 38, as timing signals through channel 34 causes lamp 38 to fire three times within a short period of time, preferably at least one millisecond between strobes in order to ensure that the flashlamp remains stable. High speed discharge circuits capable of providing three flashes within such a short time are critical to ensuring high system throughput. One example of such a high speed discharge circuit is provided in co-pending pending U.S. patent application Ser. No. 09/521,753 filed Mar. 9, 2000, entitled "Rapid Firing Flashlamp Discharge Circuit" assigned to the assignee of the present invention and herein incorporated by reference, now abandoned. Other types of illumination sources are usable with the present invention, such as a pulsed laser or a pulsed LED, as long they are able to provide a short duration, high energy successive pulses within the preferred time period. Condenser lens 40 collects light from the flashlamp 38 and directs it through reticle 41 to the projector lens 42, which forms a sinusoidally varying fringe image on the solder deposits 36. Preferably, reticle 41 has an astigmatic pattern and the projector lens is astigmatic, together reliably forming sinusoidally varying astigmatic patterns with low harmonic distortion as shown in FIG. 2.

Projector lens system 28 is preferably doubly telecentric, in that it is telecentric in reticle space and target space (at solder paste deposits 36 on board 22). The double telecentricity is important since it allows the height, volume and area calculations to be independent of the location of the solder paste within the field of view and depth of focus. This characteristic also provides lower distortion for the system as a whole, which is important because the target moves between exposures.

Camera system 30 views the projected fringes on the target of solder paste deposits 36, and acquires and digitizes images in rapid succession. Camera system 30 does not include a grating, as is incorporated in moire interferometry systems. Preferably, camera system 30 is telecentric in target space and has low distortion for the same reasons given above. The field of view of camera system 30 is approximately 10 mm in the y direction and 20 mm in the x direction. The size of the field of view is selected to maximize the field coverage while still maintaining sufficient resolution of the target. CCD array 46 is a megapixel array and as such is able to inspect solder paste features of fine detail. For example, solder features for components such as a Chip Scale Package (CSP) or a microball grid array can be inspected. However, by sampling or combining individual pixels, larger equivalent pixels are generated which facilitates inspection at higher speeds. One way that such sampling is done is by decimating the photo-charge of four pixels into an equivalent pixel within CCD array 46 itself. This decimation provides a faster CCD image readout rate than that attainable with standard resolution (two times faster) and thus reduces subsequent processing time. In the preferred embodiment, the inspection mode can be rapidly switched between the high-resolution mode and the high-speed mode for different solder paste features on the same board, based upon the type of components that will be found in different areas of board 22. As such, optical sensor system 18 employs a dual-resolution capability in the same unit.

CCD 46 is a 1024×1024 pixel area array CCD image sensor, where each pixel generates charge in response to light exposure. In the preferred embodiment CCD array 46 is a multi-tap CCD array providing image data through four taps at a rate of 20 megapixels per second, per tap. Thus, CCD array 46 is able to provide image data at a rate of 80 megapixels per second. CCD array 46 can be a commercially available CCD array such as the model THX7888, available from Thomson-CSF Semiconductor. Preferably, camera system 30 samples the target at a pitch of 20 microns square on the target surface.

Circular illuminator 26 receives illumination control signals from processor 14 through illumination control channel 34 and are essential in properly illuminating fiducial marks 32. Once located, the fiducial marks provide a circuit board frame of reference for locating other features on board 32. Illuminator 26 preferably includes a plurality of diffuse LEDs which cast diffuse illumination on circuit board 22. Illuminator 26 also preferably comprises LEDs that are oriented to direct near specular illumination upon marks 32. Both diffuse illumination and near specular illumination are used in the imaging.

Laser range finder 29 is a low power laser rated no higher than Class II, which projects a spot onto the target which is viewed by camera system 30. Laser 29 can be of such a low power because its sole function is measuring the range to the target in order to establish system focus. Before any of the triply exposed fringe images are acquired, the range to the target from finder 29 is measured. The choice of a Class II laser is preferable in view of more stringent FDA safety precautions for Class III lasers. Such safety precautions add unnecessary complexity to the use of the solder paste inspection system.

Figure 3:
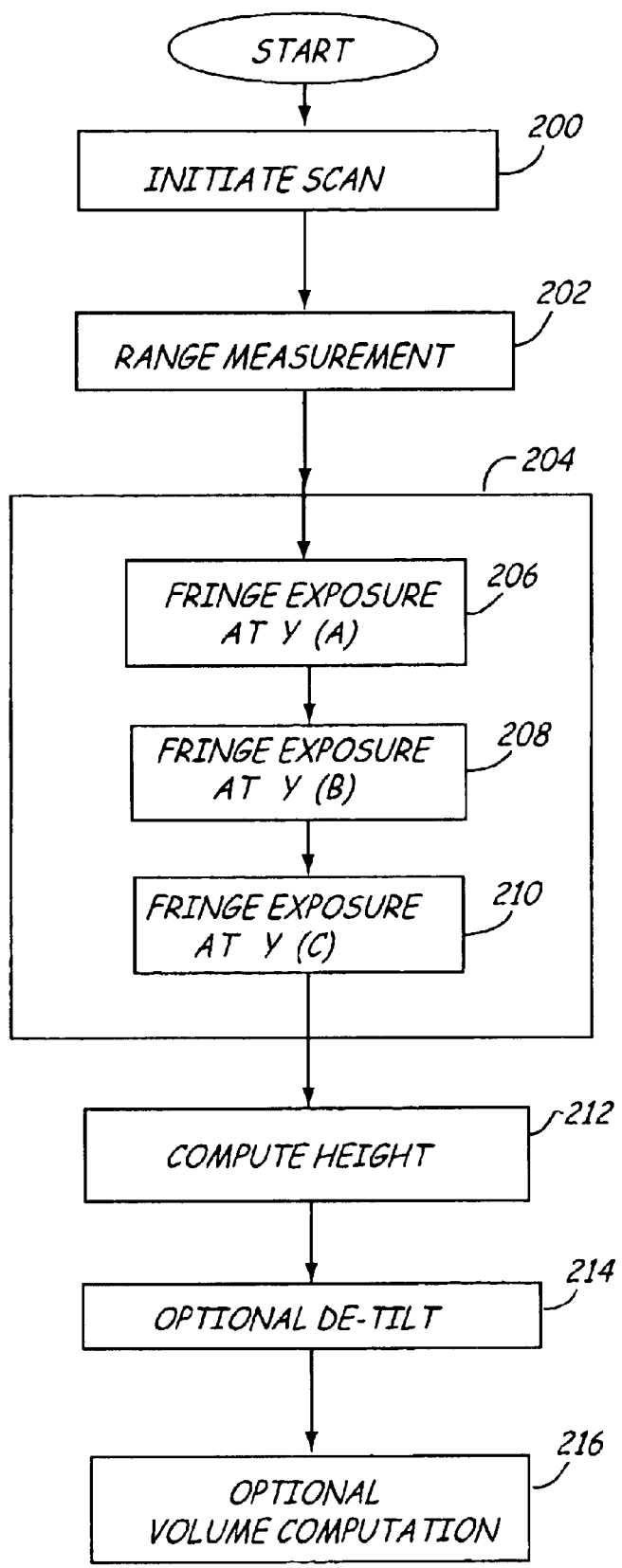
FIG. 3 is a block diagram of the method of the present invention.

System 10 is characterized by continuous X-Y stage motion while inspection occurs, as shown in FIG. 3. In operation, at box 200 computer 12 sends instructions to initiate X-Y stage 16 movement to scan desired solder paste area 36. In the preferred embodiment, four exposures occur for each height computation; three images, each of a different phase, to be used in height computation and one image of the laser spot for focus control. It is understood that the present invention contemplates the use of sets of two, three or more images, each set having images of a different phase, for use in constructing a height map. The discussion below concentrates on the three image, preferred embodiment, height computation. The first exposure is from range finder 29, which illuminates the target with a laser spot and hence exposes CCD 46 in camera system 30, at box 202. The measurement from range finder 29 dictates the amount of z movement for focus adjustment. Next, three successive exposures of fringe patterns of the target occur at each of three distinct positions which are separated by an integral number of target pixel boundaries, so that the difference in phase between each of the successive exposures is approximately 120 degrees (box 204). Specifically, at box 206, the first fringe exposure is made at position y(a) and CCD 46 acquires an image of the target 36. Stage 16 continues to move, and at position y(b), the second fringe exposure is made and CCD 46 acquires another image of the target 36 (box 208). Stage 16 continues to move, and at position y(c), the third fringe exposure is made and CCD 46 acquires another image of the target 36 (box 210). The velocity of motion and the spacing between exposures is such that the three exposures in box 204 have occurred within approximately 2 milliseconds, which allows the system to be substantially insensitive to vibration. The strobe lamp provides illumination of such short duration that none of the three images have any appreciable blurring due to the continuous motion. The three exposures have been taken as a function of stage 16 position, so that the distance between exposures is preferably an integral number of target pixels, where a "target pixel" is the area which is imaged by a pixel in CCD 46. Preferably, the stage movement between exposures is seven integral pixels, although other distances are suitable for use with the present invention. Additionally, while the preferred embodiment is to shift the stage by an integral number of pixels for computational efficiency, non-integral numbers can be used with equal ease but with less straightforward computations.

Additionally, rapidly pulsing strobe lamp 38 essentially freezes the image of feature 36 even as system 18 and target 36 move relative to each other. Such freezing eliminates the time previously required for prior art systems to stop and shoot multiple images, so as to increase system throughput.

In a preferred embodiment of the present invention, the images from each of the exposures 206, 208, 210 are stored in CCD 46 and then transferred to processor 14. Typical CCD operation does not occur quickly enough to acquire three images while maintaining suitable vibration immunity. However, a method of rapidly acquiring three images in a CCD frame array is provided in co-pending U.S. patent application Ser. No. 09/522,519, filed Mar. 10, 2000, entitled "Inspection System With Vibration Resistant Video Capture," assigned to the assignee of the present invention and incorporated herein by reference, now U.S. Pat. No. 6,549,647. However, the present invention is not limited to such data storage and subsequent transfer. For example, the invention is equally well suited to real time transfer of the image data after each of the exposures is made.

Camera system 30 provides analog data to analog/digital electronics 48. The image data is provided to analog/digital electronics for conversion into digital form, and provided to processor 14 through digital video channel 52.

At box 212, height is computed according to the equations described below, which is described in terms of the three exposures taken in the preferred embodiment. The processor receives three digitized images from camera system 30. Preferably, the images are digitized before leaving housing 18. In order to compute the height image, H, processor 14 first co-sites the images to make a correspondence between each of the three pixels (one in each image) corresponding to the same physical location. Co-siting is accomplished by offsetting an acquired digitized image by a distance corresponding to the stage movement, and the three resulting co-sited images are called A, B and C in the discussion below.

A generalized approach allows us to compute H from images where the phase differences between successive images are known but unequal. The normalized intensity value for each pixel in the three-image co-sited set is given in Equation 1):

$$\begin{pmatrix} A \\ B \\ C \end{pmatrix} = r \begin{pmatrix} 1 + m\cos(\phi - \phi_a) \\ 1 + m\cos(\phi - \phi_b) \\ 1 + m\cos(\phi - \phi_c) \end{pmatrix} \quad (1)$$

where r is the normalized reflectance at the pixel, the known phase angles of the three fringes are $\phi_a$, $\phi_b$, $\phi_c$, and the relative phase $\phi$ of the fringe at the pixel is related to the projected fringe frequencies, pixel coordinate and z position by Equation 2):

$$\phi = 2\pi(f_x x + f_y y + f_z z) \quad (2)$$

To linearize the problem and make it more easily computed, the quantities are defined as in Equation 3):

$$x = rm \cos \phi$$
$$y = rm \sin \phi \quad (3)$$

Then, Equation 1) can be re-written as in Equation 4):

$$\begin{pmatrix} A \\ B \\ C \end{pmatrix} = \begin{pmatrix} 1 & \cos\phi_a & \sin\phi_a \\ 1 & \cos\phi_b & \sin\phi_b \\ 1 & \cos\phi_c & \sin\phi_c \end{pmatrix} \begin{pmatrix} r \\ x \\ y \end{pmatrix} \quad (4)$$

Through standard linear algebra, the system matrix in Equation 4) can be solved for r, x, and y. From x, y, the phase $\phi$ of the pixel can be computed by the processor in Equation 5):

$$\phi = \tan^{-1}(y/x) \quad (5)$$

Figure 4A:
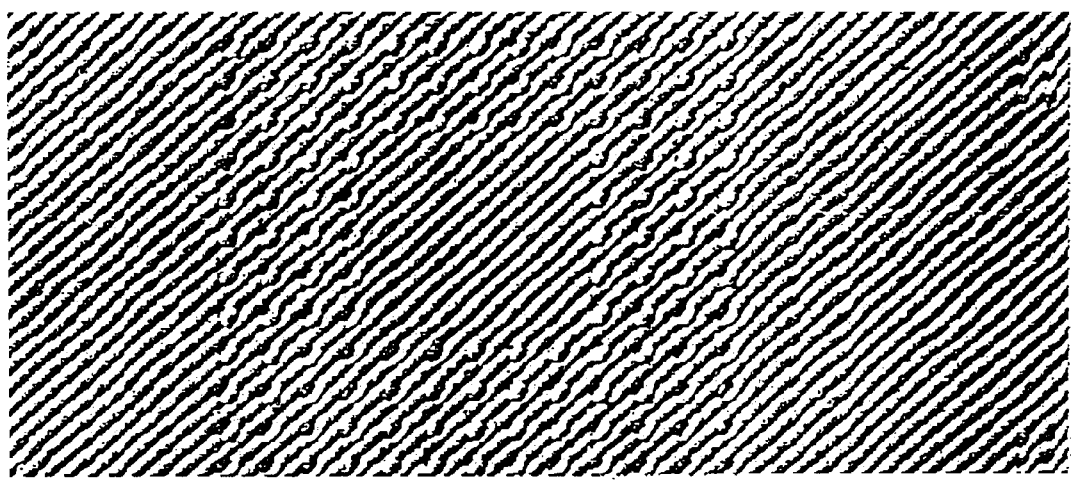
FIG. 4A is a map of the height of the target, before the de-tilt compensation is performed.

Once the phase $\phi$ is computed in Equation 5), we multiply by an appropriate calibration scaling factor to compute the height of the pixel. Once all the heights for all the pixels are computed, the height map, H, is completed and ready for summary processing and display, as appropriate. An example height map is shown in FIG. 4A.

Figure 4B:
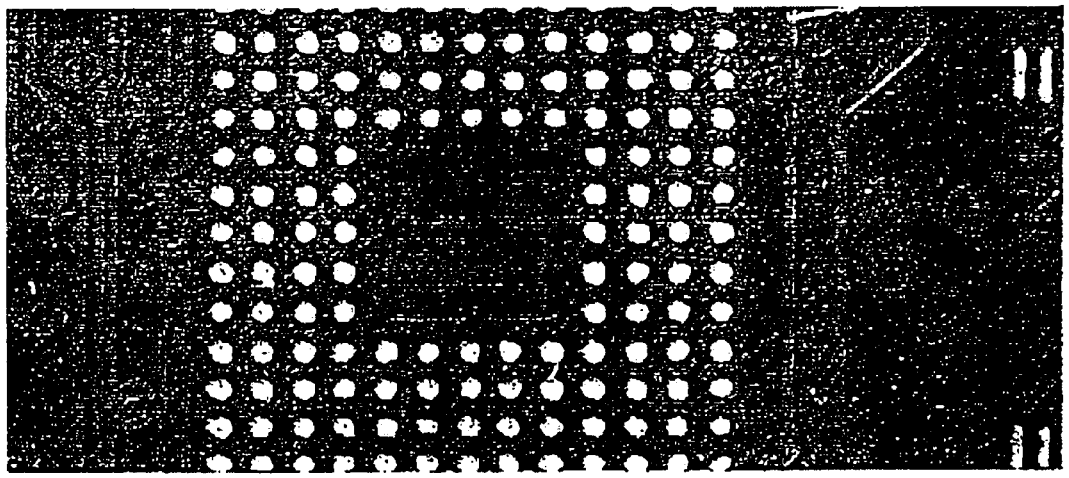
FIG. 4B is a height map after de-tilting compensation is performed.

Once the height map, H, of the surface of interest is constructed, microprocessor 12 optionally corrects the height map for the tilt, in a process known as de-tilting the substrate (box 214). An example de-tilted height map corresponding to the image in FIG. 4A is shown in FIG. 4B. In the past, it was necessary for users to enter a number of program points in order to help the inspection system establish a reference plane for subsequent measurements. In the preferred embodiment, such user-intervention is rendered unnecessary by using the method provided in co-pending U.S. patent application Ser. No. 08/607,846, filed Feb. 27, 1996, entitled "Apparatus and Method for Estimating Background Tilt and Offset," assigned to the assignee of the present application, and incorporated herein by reference. Other de-tilt algorithms are equally applicable for use in the present invention.

Preferably, processor 14 performs a number of compensatory functions. In particular, processor 14 corrects for errors in the gain and offset of CCD 46 on a pixel by pixel basis, in addition to correcting for variations in the illumination field provided by projection system 28. Processor 14 also corrects for Z wrap caused by optical distortion in projection system 28 and camera 30. Finally, processor 14 corrects for strobe to strobe variation in gross energy output.

Finally, computer 12 computes the volume of individual solder paste deposits, as the edges of the deposits are also known, at least from the height map (box 216).

Although the present invention has been described with respect to preferred embodiments, changes can be made in form and detail without departing from the spirit and scope of the invention. In particular, while the present invention is disclosed in terms of the preferred embodiment of three exposures for use in constructing a height map, it is understood that the apparatus and methods disclosed are equally well suited (with appropriate modifications for height computation, co-siting algorithms and the like) for use in constructing a height map using two phases, as well as the use of four or more phases.

What is claimed is:

1. An inspection system for inspecting an article of manufacture such as a printed circuit board, the system comprising:
    a strobed illuminator adapted to project light through a reticle so as to project a pattern of light onto an area of the printed circuit board;
    a board transport responsively positioning the board to at least two distinct positions, each position corresponding to a different phase of the projected light;
    a detector adapted to acquire at least two images of the area, each image corresponding to one of the at least two different phases;
    an encoder outputting a position output; and
    a processor coupled to the encoder, the board transport, the illuminator and the detector, the processor adapted to controlledly energize the illuminator to expose the area as a function of the position output, the processor co-siting the at least two images and to construct a height map image with the co-sited images.

2. The system of claim 1 where the inspection system inspects solder paste deposits.

3. The system of claim 1, wherein the strobed illuminator is energized at least two times within a fixed period of time.

4. The system of claim 3, wherein the fixed period of time is approximately one millisecond.

5. The system of claim 4, wherein the approximately one millisecond separation provides improved immunity from vibration of the board.

6. The system of claim 1, wherein:
    the detector is further adapted to acquire an additional image of the area; and
    the processor operates upon three images of the area to provide the compensated height map.

7. The system of claim 1, wherein the processor further comprises a circuit for compensating the height map for a tilt with respect to a reference plane.

8. The system of claim 1, wherein the detector includes a plurality of pixels, and further that the detector is operable in a first and a second mode, the second mode accomplished by decimating charge from the pixels into an equivalent charge for an equivalent pixel, where the equivalent pixel is larger in effective area than the pixel.

9. The system of claim 8, wherein the plurality of pixels is 4.

10. The system of claim 8, wherein each pixel has a length of about 20 microns.

11. The system of claim 8, wherein the equivalent pixel has a length of about 40 microns.

12. The system of claim 8, wherein the processor is further adapted to select between the first and second modes based upon a characteristic of the area.

13. The system of claim 12, wherein the characteristic is a known component type to be placed on the area.

14. The system of claim 1, wherein the illuminator comprises a white strobe lamp.

15. The system of claim 1, wherein the illuminator comprises a short duration, high power pulsed lamp.

16. A method for inspecting a target, the method comprising:

illuminating a solder paste feature with a pattern of light;

encoding an x-y position of the target;

acquiring at least two images of the target at two distinct x-y positions of the target, the two images acquired as a function of the target position; and calculating a height of the target based upon the at least two acquired images.

17. The method of claim 16, further comprising acquiring an additional image of the target at another distinct position of the target, where the step of calculating the height is computed as a function of the at least two acquired images and the additional image.

18. An inspection system for inspecting an article of manufacture such as a printed circuit board, the system comprising:

an illuminator adapted to project light through a reticle so as to project a pattern of light onto an area of the printed circuit board;

a board transport responsively positioning the board to at least two distinct positions, each position corresponding to a different phase of the projected light;

a detector having an optical axis and being adapted to acquire at least two images of the area, each image corresponding to one of the at least two different phases, wherein the area is displaced in a direction having a component perpendicular to the optical axis between acquisition of the at least two images;

an encoder outputting a position output; and a processor coupled to the encoder, the board transport, the illuminator and the detector, the processor adapted to controlledly energize the illuminator to expose the area as a function of the position output, the processor co-siting the at least two images and to construct a height map image with the co-sited images.

19. The system of claim 18, wherein the illuminator is a strobed illuminator, and wherein the detector acquires the at least two images during relative motion between the detector and the area.

20. An inspection system for inspecting an article of manufacture such as a printed circuit board, the system comprising:

a strobed illuminator adapted to project light through a reticle so as to project a pattern of light onto an area of the printed circuit board, at an angle relative to the printed circuit board;

a board transport responsively positioning the board to at least two distinct positions, each position corresponding to a different phase of the projected light;

a detector having an optical axis disposed to view the area from an angle different than the angle of illumination, the detector being adapted to acquire at least two images of the area, each image corresponding to one of the at least two different phases;

an encoder outputting a position output; and a processor coupled to the encoder, the board transport, the illuminator and the detector, the processor adapted to controlledly energize the illuminator to expose the area as a function of the position output, the processor co-siting the at least two images and to construct a height map image with the co-sited images.

\* \* \* \* \*

UNITED STATES PATENT AND TRADEMARK OFFICE
CERTIFICATE OF CORRECTION

PATENT NO. : 6,750,899 B1  
DATED : June 15, 2004  
INVENTOR(S) : Fishbaine et al.

It is certified that error appears in the above-identified patent and that said Letters Patent is hereby corrected as shown below:

<u>Title page,</u>  
Item [56], References Cited, insert:

-- U.S. PATENT DOCUMENTS

| | | | |
|---|---|---|---|
| 5,069,548 | 12/03/91 | Boehnlien | 356/376 |
| 5,298,734 | 03/29/94 | Kokubo | 250/208.1 |
| 5,307,152 | 04/26/94 | Boehnlein et al. | 356/376 |
| 5,744,221 | 06/30/98 | Guerra | 356/376 |
| 5,969,819 | 10/19/99 | Wang | 356/371 |
| 6,084,712 | 07/04/00 | Harding | 359/618 |
| 6,232,724 | 05/15/01 | Onimoto et al. | 315/161 |
| 6,268,923 | 07/32/01 | Michniewicz et al. | 356/512 |
| 6,307,210 | 10/23/01 | Suzuki et al. | 250/599.08 |
| 5,555,090 | 09/10/96 | Schmutz | 356/381 |
| 2,625,856 | 01/20/53 | Muller | |
| 5,406,372 | 04/11/95 | Vodanovic et al. | 356/394 |
| 5,668,665 | 09/16/97 | Choate | 359/663 |
| 5,691,784 | 11/25/97 | Hausler et al. | 349/1 |
| 5,708,532 | 01/13/98 | Wartmann | 359/663 |
| 5,867,604 | 02/02/99 | Ben-Levy et al. | 382/254 |
| 5,953,448 | 07/14/99 | Liang | 382/154 |
| 5,039,868 | 08/13/91 | Kobayashi et al. | 250/572 |
| 5,091,963 | 02/25/92 | Litt et al. | 382/8 |
| 5,103,105 | 04/07/92 | Ikegaya et al. | 250/561 |
| 5,684,530 | 11/04/97 | White | 348/131 |
| 5,686,994 | 11/11/97 | Tokura | 356/394 |
| 5,761,337 | 06/02/98 | Nishimura et al. | 382/150 |
| 5,912,984 | 06/15/99 | Michael et al. | 382/149 |
| | | | |
| 09/522,519 | 03/10/00 | Skunes et al. | |
| 09/754,991 | 01/05/01 | Kranz et al. | -- |

Signed and Sealed this

Twenty-eighth Day of December, 2004

JON W. DUDAS  
*Director of the United States Patent and Trademark Office*

UNITED STATES PATENT AND TRADEMARK OFFICE
CERTIFICATE OF CORRECTION

PATENT NO. : 6,750,899 B1
DATED : June 15, 2004
INVENTOR(S) : Fishbaine et al.

It is certified that error appears in the above-identified patent and that said Letters Patent is hereby corrected as shown below:

<u>Title page,</u>
Item [56], References Cited, insert:

-- U.S. PATENT DOCUMENTS

| | | | |
|---|---|---|---|
| 5,069,548 | 12/03/91 | Boehnlien | 356/376 |
| 5,298,734 | 03/29/94 | Kokubo | 250/208.1 |
| 5,307,152 | 04/26/94 | Boehnlein et al. | 356/376 |
| 5,744,221 | 06/30/98 | Guerra | 356/376 |
| 5,969,819 | 10/19/99 | Wang | 356/371 |
| 6,084,712 | 07/04/00 | Harding | 359/618 |
| 6,232,724 | 05/15/01 | Onimoto et al. | 315/161 |
| 6,268,923 | 07/32/01 | Michniewicz et al. | 356/512 |
| 6,307,210 | 10/23/01 | Suzuki et al. | 250/599.08 |
| 5,555,090 | 09/10/96 | Schmutz | 356/381 |
| 2,625,856 | 01/20/53 | Muller | |
| 5,406,372 | 04/11/95 | Vodanovic et al. | 356/394 |
| 5,668,665 | 09/16/97 | Choate | 359/663 |
| 5,691,784 | 11/25/97 | Hausler et al. | 349/1 |
| 5,708,532 | 01/13/98 | Wartmann | 359/663 |
| 5,867,604 | 02/02/99 | Ben-Levy et al. | 382/254 |
| 5,953,448 | 07/14/99 | Liang | 382/154 |
| 5,039,868 | 08/13/91 | Kobayashi et al. | 250/572 |
| 5,091,963 | 02/25/92 | Litt et al. | 382/8 |
| 5,103,105 | 04/07/92 | Ikegaya et al. | 250/561 |
| 5,684,530 | 11/04/97 | White | 348/131 |
| 5,686,994 | 11/11/97 | Tokura | 356/394 |
| 5,761,337 | 06/02/98 | Nishimura et al. | 382/150 |
| 5,912,984 | 06/15/99 | Michael et al. | 382/149 |
| 09/522,519 | 03/10/00 | Skunes et al. | |
| 09/754,991 | 01/05/01 | Kranz et al. | |
| 4,782,394 | 11/01/88 | Hieda et al. | 358/213.19 |
| 5,298,734 | 03/29/94 | Kokubo | 250/208.1 |
| 5,546,127 | 08/13/96 | Yamashita et al. | 348/297 |
| 5,982,927 | 11/09/99 | Koljonen | 382/168 |
| 5,999,266 | 12/07/99 | Takahashi et al. | 356/376 |
| 6,061,476 | 05/09/00 | Nichani | 382/270 |
| 6,180,935 | 01/30/01 | Hoagland | 250/208 |
| 6,268,923 | 07/31/01 | Michniewicz et al. | 356/512 |
| 6,269,197 | 07/31/01 | Wallack | 382/285 |
| 5,815,275 | 09/29/98 | Svetkoff et al. | 356/376 |
| 5,455,870 | 10/03/95 | Sepai et al. | 382/147 |
| 5,424,552 | 06/13/95 | Tsuji et al. | 250/548 |

UNITED STATES PATENT AND TRADEMARK OFFICE
CERTIFICATE OF CORRECTION

PATENT NO.   : 6,750,899 B1
DATED        : June 15, 2004
INVENTOR(S)  : Fishbaine et al.

It is certified that error appears in the above-identified patent and that said Letters Patent is hereby corrected as shown below:

References Cited, (cont.)
FOREIGN PATENT DOCUMENTS

| | | |
|---|---|---|
| DE 4011407 | 10/10/91 | Germany |
| WO 99/12001 | 03/11/99 | WIPO |
| WO 02/01209 A1 | 01/03/02 | WIPO |
| WO 02/01210 A1 | 01/03/02 | WIPO |
| WO 0154068 A2 | 07/26/01 | WIPO |
| EP 0660 078 A1 | 12/11/94 | EPO |
| WO 99/24786 | 05/20/99 | WIPO |
| DE 40 11 407 A1 | 10/10/91 | Germany |
| EP 0 453 977 A2 | 10/30/91 | EPO |

OTHER ART

Copy of International Search Report from Application Number PCT/US00/42764 with international filing date of December 12, 2000.
Copy of International Search Report from Application Number PCT/US01/00330 with international filing date of May 1, 2001.

This certificate supersedes Certificate of Correction issued Decemeber 28, 2004.

Signed and Sealed this

Fourteenth Day of June, 2005

JON W. DUDAS
*Director of the United States Patent and Trademark Office*